US00PP37009P2

(12) United States Plant Patent
Radler

(10) Patent No.: US PP37,009 P2
(45) Date of Patent: Oct. 14, 2025

(54) SHRUB ROSE PLANT NAMED 'RADMEADOW'

(50) Latin Name: *Rosa hybrida*
Varietal Denomination: Radmeadow

(71) Applicant: The Conard Pyle Company, West Grove, PA (US)

(72) Inventor: William Radler, Greenfield, WI (US)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 19/004,780

(22) Filed: Dec. 30, 2024

(51) Int. Cl.
*A01H 6/74* (2018.01)
*A01H 5/02* (2018.01)

(52) U.S. Cl.
USPC ..... Plt./102

(58) Field of Classification Search
USPC ..... Plt./102
CPC ..... A01H 6/749; A01H 5/02; A01H 6/74
See application file for complete search history.

(56) References Cited

U.S. PATENT DOCUMENTS

PP19,362 P2 10/2008 Kordes
PP26,790 P3 6/2016 Meilland et al.

OTHER PUBLICATIONS

Enchanted Meadow, Heirloom Roses, https://heirloomroses.com/products/enchanted-meadow (downloaded Dec. 30, 2024).
Rosa Enchanted Meadow ('Radmeadow'), Prides Corner Farms https://www.pridescorner.com/plant-name/ROSA-ENCHANTED-MEADOW (downloaded Dec. 30, 2024).

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of shrub rose plant, referred to by its cultivar name, 'Radmeadow', is described. The new variety forms in abundance on a substantially continuous basis, bicolor cream and pink-colored blossoms. The growth habit is very bushy and rounded. Semi-glossy, dark green ornamental foliage is formed. Additionally, the new variety is particularly well suited for growing as distinctive ornamentation in the landscape.

1 Drawing Sheet

Latin name of genus and species of plant claimed: *Rosa hybrida.*
Variety denomination: 'Radmeadow'.

STATEMENT REGARDING PRIOR DISCLOSURES BY THE INVENTOR

The first offer for sale of the new variety was Spring of 2024 through the Prides Corner Farms website and Heirloom Roses website. The first sale or offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of shrub rose plant of the present invention was created by controlled breeding during June 2013, in Milwaukee, Wisconsin by artificial pollination wherein two parents were crossed which previously had been studied in the hope that they would contribute the desired characteristics. The female parent (i.e., the seed parent) of the new variety was an unnamed breeder seedling (not patented). The male parent (i.e., the pollen parent) of the new variety was the 'KORfloci08' variety (U.S. Plant Pat. No. 19,362).

The parentage of the new variety can be summarized as follows:

unnamed breeder seedling x 'KORfloci08'

The seeds resulting from the above pollination were sown and small plants were obtained which were physically and biologically different from each other. Selective study resulted in the identification of a single plant of the new variety.

The new variety has been found to undergo asexual propagation in Wasco, California and Cochranville, Pennsylvania by a number of routes such as vegetative cuttings. Asexual propagation techniques in Wasco, California and Cochranville, Pennsylvania, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of shrub rose plant of the present invention possesses the following combination of characteristics:

(a) forms bicolor cream and pink colored blossoms,
(b) exhibits a very bushy and rounded growth habit, and
(c) forms semi-glossy and dark green colored foliage.

The new variety well meets the needs of the horticultural industry. It can be grown to advantage as ornamentation in parks, gardens, public areas, and residential landscapes. Accordingly, it is particularly well suited for growing in the landscape.

The new variety can be readily distinguished from its ancestors. More specifically, the new variety provides bicolor cream and pink colored blossoms and stronger peduncles compared to the pale pink colored blossoms of the unnamed breeder seedling parent (i.e., the seed parent). Additionally, the new variety displays a slightly larger growth habit, longer bloom life, and bicolor cream and pink colored flowers, compared to the 'KORfloci08' variety (i.e., the pollen parent) which displays orange-red colored flowers. Moreover, the new variety can be readily distinguished from non-parental related similar varieties. For example, the new variety displays cream-colored flowers with pink margins compared to the white colored blossoms of the 'Meiradena' variety (U.S. Plant Pat. No. 26,790).

The new variety has been named the 'Radmeadow' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new variety. The illustrated rose plant of the new variety was approximately two years of age and was grown outdoors on its own roots in a one-gallon container in Cochranville, Pennsylvania in May 2024.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on a two-years-old specimen of the new variety, observed during September 2023, while growing in a three-gallon container on its own roots in a greenhouse in Cochranville, Pennsylvania.

Botanical classification: *Rosa hybrida* cultivar 'Radmeadow'.

Commercial classification: Shrub Rose.

Plant:

*Habit*.—Very bushy and rounded.

*Height*.—Approximately 60.0 cm on average from the top of the soil plane.

*Width*.—Approximately 50.0 cm on average.

Branches:

*Stem color*.—Old wood: Greyed-Green Group 197A. — young stems: Green Group 142A.

*Length*.—Main stems: approximately 40.0 cm on average. — secondary stems: approximately 30.0 cm on average.

*Diameter*.—Main stems: approximately 1.5 cm on average. — secondary stems: approximately 5.0 mm on average.

*Texture*.—Smooth.

*Prickles*.—Amount: moderate, 3 to 4 per internode. — young prickles: length is approximately 6.0 mm on average; width is approximately 3.0 mm on average at point of attachment; and color is Greyed-Orange Group 174A and Yellow-Green Group N144B. — old prickles: length is approximately 6.0 mm on average; width is approximately 4.0 mm on average at point of attachment; and color is Grey-Brown Group 199B.

Leaflets:

*Number*.—3, 5, and 7.

*Shape*.—Ovate; apex is acute to acuminate; and base is cuneate.

*Arrangement*.—Odd-pinnate.

*Margin*.—Serrate.

*Undulation*.—Moderate.

*Glossiness of upper side*.—Semi-glossy.

*Texture*.—Upper surface: smooth. — under surface: smooth.

*Venation pattern*.—Reticulate.

*Size*.—Terminal leaflet: length is approximately 5.0 cm on average; width is approximately 3.0 cm on average. — lower leaflets: length is approximately 3.0 cm on average; width is approximately 2.1 cm on average. — 5-Leaflet leaf. length is approximately 10.0 cm on average; width is approximately 7.0 cm on average.

Foliage:

*Young foliage*.—Upper surface color: Green Group 143A edged with Red-Purple Group 61A with indistinguishable venation. — under surface color: Yellow-Green Group 146C edged with Red-Purple Group 61A with indistinguishable venation.

*Old foliage*.—Upper surface color: Green Group 137C with indistinguishable venation. — under surface color: Green Group 138B with indistinguishable venation.

*Petiole*.—Texture: upper surface is hispid; under surface is mostly smooth with a few thorny protrusions. — length: approximately 2.2 cm on average. — width: approximately 1.0 mm on average. — upper surface color: Green Group 143A with Red-Purple Group 60A down the center. — under surface color: Green Group 143C.

*Rachis*.—Length: approximately 1.6 cm on average. — width: approximately 1.0 mm on average. — upper surface color: Green Group 138A. — under surface color: Green Group 143C.

*Stipules*.—Length: approximately 1.5 cm on average. — width: approximately 7.0 mm on average. — margin: entire to erose. — upper surface color: Green Group 143A. — lower surface color: Green Group 143C.

Inflorescence:

*Number of flowers*.—About 28 to 30 blooms on average on a plant at once.

*Number of blossoms per stem or in a cluster*.—Typically 1 bloom per stem on average.

*Peduncle*.—Color: Green Group 143A. — diameter: approximately 3.0 mm on average. — length: approximately 4.0 cm on average. — surface texture: hispid.

*Sepals*.—Number: 4 to 5. — upper surface color and texture: Green Group 143C, covered in short pubescence. — under surface color and texture: Yellow- Green Group 144A, hispid. — size: length is approximately 3.0 cm on average; width is approximately 8.0 mm on average. — margin: entire with extensions on two or three sepals measuring approximately 3.0 mm in length and 1.0 mm in width on average. — apex: acute to aristate. — base: truncate as it joins the receptacle.

*Buds*.—Shape: ovoid. — size: length is approximately 3.0 cm on average; width is approximately 1.0 cm on average. — color (when opening): Yellow Group 8B and Red Group N45D.

*Flower*.—Form: double, cuplike. — profile: flat to slightly concave as it opens. — diameter: approximately 5.5 cm on average. — height: approximately 2.5 cm on average. — duration: on the plant approximately 10 to 12 days. — petal color when first and fully opened: upper surface is Green-White Group 157B with some Red-Purple Group N57A with a small basal spot of Yellow Group 4A; under surface is Orange-White Group 159C, Orange-White Group 159B with some Red-Purple Group N57A toward petal margin with a small basal spot of Yellow Group 4A. — petal color at end of bloom: upper surface is Red-Purple Group 61B transitioning to Yellow Group 4D toward point of attachment with a small basal spot of Yellow Group 4B; under surface is largely Yellow Group 4D transitioning to Red-Purple Group 61B towards petal margin with a small basal spot of Yellow Group 4B. — petals reflex one by one: yes.

*Fragrance*.—Slight sweet scent.

*Petal*.—Number: 16 to 18 on average. — drop: good. — length: approximately 3.0 cm on average. — width: approximately 3.0 cm on average. — overall shape: broadly obovate. — margin: entire with moderate undulation. — apex shape: rounded to slightly cuspidate. — base shape: cuneate. — texture: upper surface is smooth; under surface is smooth.

*Petaloids*.—Number: approximately 5 on average. — length: approximately 1.5 cm on average. — width: approximately 5.0 mm on average. — color: Yellow-White Group 158A transitioning to Green-Yellow Group 1B towards the point of attachment, with a basal spot of Yellow Group 6C. — texture: smooth. — margin: entire with slight undulation. — apex: obovate. — base: lanceolate.

*Stamen*.—Number: approximately 133.— anthers: number is approximately 133; color is Yellow-Orange Group 17A; length is approximately 2.0 mm on average; and shape is oval. — filaments: length is approximately 5.0 mm on average and color is Yellow Group 4C.

*Pistils*.—Arrangement: separate and free. — number: approximately 38. — style: length is approximately 8.0 mm on average and color is Green-Yellow Group 1A. — stigma: diameter is approximately 1.0 mm on average; shape is fan shaped; color is Yellow Group 3C.

*Receptacle*.—Diameter: approximately 5.0 mm on average. — depth: approximately 5.0 mm on average. — shape: urn shaped. — color: Yellow-Green Group 144B. — surface texture: smooth.

*Pollen*.—Amount: sparse. — color: Yellow-Orange Group 20A.

*Hips/seed*.—None observed.

Development:

*Vegetation*.—Semi-glossy, dark green, and vigorous.

*Blossoming*.—Abundant and substantially continuous from spring through frost; typically, in bloom outdoors from May to November in Southeastern Pennsylvania.

*Resistance to diseases*.—Excellent resistance for black spot (*Diplocarpon rosae*), powdery mildew (*Sphaerotheca pannosa*), and rust (*Phragmidium* sp.).

*Hardiness*.—Hardy to USDA Zone 5; further hardiness testing is in progress.

The new 'Radmeadow' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of shrub rose plant named 'Radmeadow' characterized by the following combination of characteristics:

(a) forms bicolor cream and pink colored blossoms, (b) exhibits a very bushy and rounded growth habit, and (c) forms semi-glossy and dark green colored foliage;

substantially as herein shown and described.

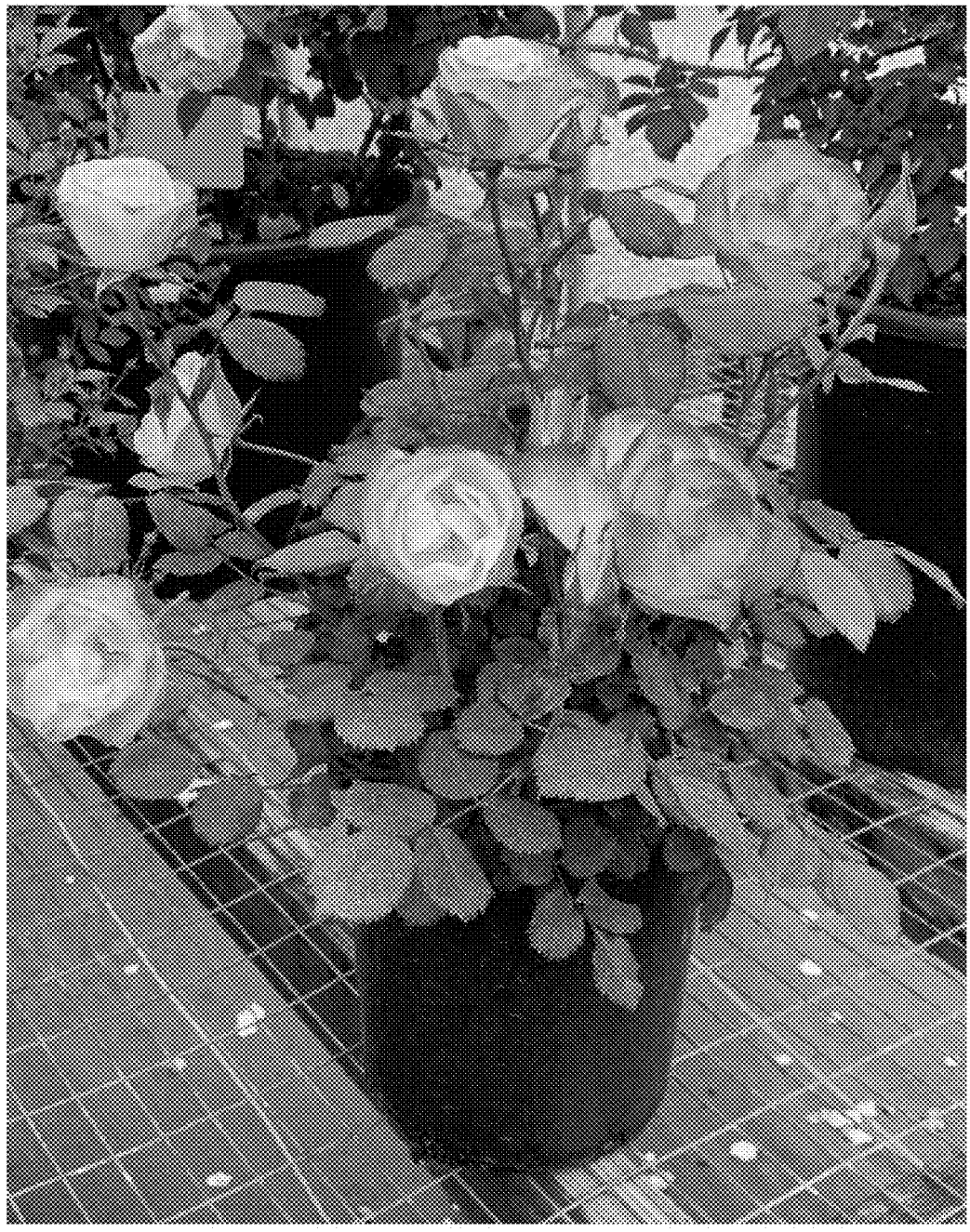

* * * * *